US012246117B2

(12) United States Patent
Singh et al.

(10) Patent No.: US 12,246,117 B2
(45) Date of Patent: Mar. 11, 2025

(54) AIR PURIFICATION DEVICES AND SYSTEMS

(71) Applicants: Uday Singh, Bloomfield, NJ (US); Steven Pirovolikos, Hempstead, NY (US); Gary DiPaolo, East Rockaway, NY (US); Juan Bernal, Clifton, NJ (US)

(72) Inventors: Uday Singh, Bloomfield, NJ (US); Steven Pirovolikos, Hempstead, NY (US); Gary DiPaolo, East Rockaway, NY (US); Juan Bernal, Clifton, NJ (US)

(*) Notice: Subject to any disclaimer, the term of this patent is extended or adjusted under 35 U.S.C. 154(b) by 662 days.

(21) Appl. No.: 17/410,710

(22) Filed: Aug. 24, 2021

(65) Prior Publication Data

US 2022/0072187 A1 Mar. 10, 2022

Related U.S. Application Data

(60) Provisional application No. 63/069,250, filed on Aug. 24, 2020.

(51) Int. Cl.
*A61L 9/20* (2006.01)
(52) U.S. Cl.
CPC .............. *A61L 9/20* (2013.01); *A61L 2209/12* (2013.01); *A61L 2209/15* (2013.01)

(58) Field of Classification Search
None
See application file for complete search history.

(56) References Cited

U.S. PATENT DOCUMENTS

| | | | | |
|---|---|---|---|---|
| 5,616,172 | A * | 4/1997 | Tuckerman | F24F 1/0071 96/57 |
| 5,837,207 | A * | 11/1998 | Summers | A61L 9/20 250/504 R |
| 6,053,968 | A * | 4/2000 | Miller | F24F 8/22 96/16 |
| 11,219,701 | B1 * | 1/2022 | Sahu | A61L 9/20 |
| 2004/0020363 | A1 * | 2/2004 | LaFerriere | B01D 46/0028 55/472 |
| 2004/0184949 | A1 * | 9/2004 | McEllen | A61L 9/20 422/4 |
| 2009/0004046 | A1 * | 1/2009 | McEllen | H05B 41/39 422/2 |

* cited by examiner

*Primary Examiner* — Jelitza M Perez

(57) ABSTRACT

A sanitizer system, comprising: a housing having an air intake end and an air outflow end; a fan disposed at the air outflow end; a cap disposed at the air intake end, the cap being coupled to an edge of the housing, the cap being spaced apart from the housing so that an intake port is formed between the cap and the housing; and an ultraviolet (UV) lamp disposed within the housing, the UV lamp being arranged to disinfect air that enters the housing through the intake port before the air is expelled by the fan through the air outflow end of the housing.

17 Claims, 16 Drawing Sheets

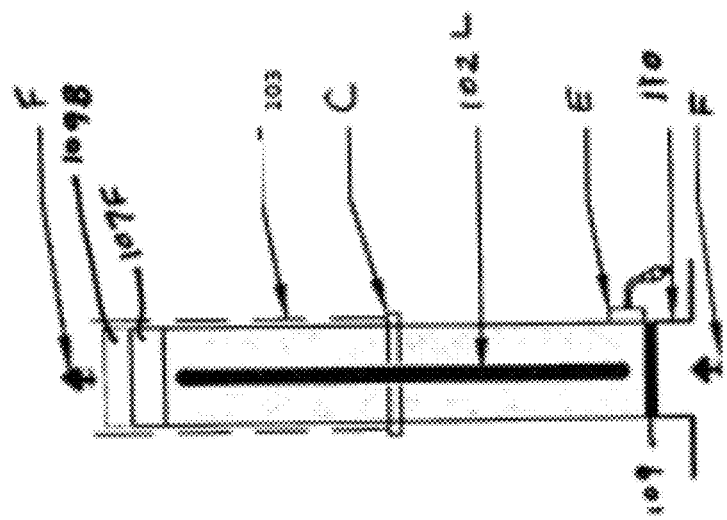
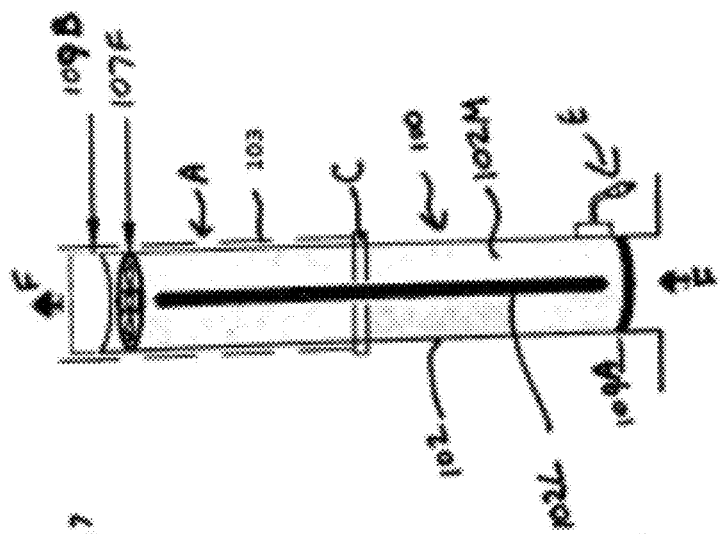
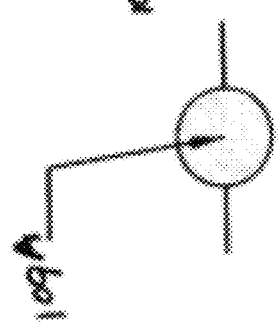

AIR PURIFICATION DEVICES AND SYSTEMS

CLAIM OF PRIORITY

The present application claims the benefit of provisional application 63/069,250, filed Aug. 24, 2020, and entitled Air Purification Devices and Systems, which is incorporated herein by reference its entirety.

BACKGROUND

Airborne pathogens are pathogens that are generated in the respiratory system and are released in exhaled air where they may be transmitted to nearby people. The efficiency by which airborne pathogens are transmitted is dependent on a variety of circumstances and air characteristics. Air characteristics that may affect the efficiency by which pathogens are spread through the air include, for example, humidity, ventilation, air speed, and/or temperature.

FIG. 1 provides a schematic illustration of the various ways in which pathogens can be spread between an infected person and a susceptible person, including close contact, airborne transmission, fomite deposits on objects or materials likely to carry infection. As illustrated, there may be a cycle through which a pathogen may travel and infect susceptible individuals. This cycle includes sharing breathed air, deposition of pathogens on surfaces, and resuspension and/or aerosolization of pathogens after such deposition such that they are once again capable of being inhaled by those in proximity. Diligent protective measures such as hand sanitization and gloves may inhibit exposure to fomites, but such measures do not address the bioaerosol that is emitted from infected individuals through such activities as talking, singing, breathing, and the like. A pathogen may remain suspended in indoor air for a duration of time that is based on the size of the pathogen and environmental factors.

Most sanitizing methods for fomites, even when effective, are time consuming and tedious to implement. In busy environments (e.g., restaurants) with high turnover of people over a relatively short duration of time, most sanitizing methods are not viable. While such methods as cleaning, disinfection, and testing might be effective in removing sanitizing surfaces, such methods are not viable or economical for many businesses (e.g., restaurants) as the effect of a disinfectant wears off after a while and could require several re-applications and require the user to perform multiple alterations to ensure effectiveness and would not be able to be performed within a reasonable amount of time.

Depending on the type of pathogen, the route by which the pathogen propagates through the air will vary. For example, it is becoming increasingly understood that with respect to SARS-Cov-2 (i.e., COVID-19), transmission is facilitated via air in inadequately ventilated environments and that the survival of the virus is negatively impacted by ozone, ultra-violet (UV) light, high temperature, and low humidity.

It is known that UV light has a germicidal effect. UV light is a form of electromagnetic radiation with a wavelength from 10 nm to 400 nm, which is shorter than that of visible light but longer than X-rays. UV light is present in sunlight and constitutes about 10% of the total electromagnetic radiation output from the Sun. Ultraviolet C (UVC) is short-wave with a wavelength between 100-280 nm, ultraviolet B (UVB) is medium-wave with a wavelength between 280 nm and 315 nm, and ultraviolet A (UVA) is long-wave with a wavelength between 315 and 400 nm. UVC light is typically used for germicidal purposes, e.g., disinfection of air and surfaces.

Shortwave UVC lamps are manufactured in a variety of ways. For example, shortwave UVC lamps may be made using a fluorescent lamp tube with no phosphor coating, composed of fused quartz since ordinary glass absorbs UVC. These are typically referred to as germicidal lamps. Such lamps emit UV light with two peaks in the UVC band at 253.7 nm and 185 nm due to mercury within the lamp, as well as some visible light. UVC light emitting diodes (LEDs) are also developing rapidly, but non-LED UV germicidal lamps are typically used for air and surface disinfection.

While some UV light require precautions to ensure safe usage because they are widely recognized for harmful effects on human skin and/or eyes, there are no work place related rules and regulations that are set by OSHA (Occupational Safety and Health Association) in regard to UVC environmental health and safety. The intensity from point sources like UVC LEDs falls off as an inverse relationship with respect to the distance squared and then falls off exponentially. Also, since the absorption length of UVC radiation is extremely short, almost no UVC radiation can reach living skin cells as all the absorption would occur in the uppermost, dead cell skin layers. Nonetheless, many have anxiety as to the potential for harmful effects of UV light generally, and it would thus be desirable that the application of such UV lights for disinfection purposes not be used in such ways that would be visible during use.

In air and surface disinfection applications the UV effectiveness is estimated by calculating the UV dose which will be delivered to the microbial population. The UV dose is calculated as follows:

$$\text{UV dose } (\mu W \cdot s/cm^2) = \text{UV intensity } (\mu W/cm^2) \times \text{exposure time (seconds)}$$

Disinfection using UVC light is thus dependent on such factors as the intensity of the UVC light and the exposure time. In addition, when attempting to use UVC light for disinfection, proper placement of the light it is also important. For example, when UVC light is being used to disinfect air, air must flow in such a way such that it is exposed to the UVC light for a sufficient length of time to have the germicidal effect.

Unlike air filters like HEPA filters, which attempt to capture fine particles, UVC germicidal lights attempt to neutralize pathogens found in the air, and for certain applications, UVC light may be preferable to HEPA filters for a variety of reasons. For example, HEPA filters typically are capable of filtering particles that have diameters that are greater than or equal to 0.3 μm. However, the smallest coronavirus particles are about 0.06 μm and the largest are about 0.15 μm, and the smaller the particle size, the longer the particle remains in the air. For example, a spherical of 4 μm in diameter may remain airborne for up to 33 minutes in still air as compared to a 1 μm particle that will take 8 hours to settle. Often filtration and purification devices are placed on the floor. Considering the filtration limitations of HEPA filters and the placement of the HEPA filter, conventional HEPA filters may be ineffective or insufficient in isolation to purify the air in a timely and efficient manner.

Accordingly, the present disclosure now recognizes that there is a need for improved systems and devices that facilitate purification of the air in common spaces so that the possibility of spreading germs is lessened, for example, by improving the efficiency of air purification and by facilitating better placement of the purification device to better facilitate air purification.

It should be noted that the foregoing background section is provided to better facilitate an understanding of the present disclosure. The discussion throughout this specification comes about due to the realization of the inventor and/or the identification of certain related art problems by the inventor and, moreover, any discussion of documents, devices, acts or knowledge in this specification is included to explain the context of the invention. It should not be taken as an admission that any of the material forms a part of the prior art base or the common general knowledge in the relevant art on or before the priority date of the disclosure and claims herein.

SUMMARY

According to aspects of the disclosure, a sanitizer system is provided, comprising: a housing having an air intake end and an air outflow end; a fan disposed at the air outflow end; a cap disposed at the air intake end, the cap being coupled to an edge of the housing, the cap being spaced apart from the housing so that an intake port is formed between the cap and the housing; and an ultraviolet (UV) lamp disposed within the housing, the UV lamp being arranged to disinfect air that enters the housing through the intake port before the air is expelled by the fan through the air outflow end of the housing.

According to aspects of the disclosure, a sanitizer system is provided, comprising: a housing having an air intake end and an air outflow end; a fan disposed at the air outflow end; a cap disposed at the air intake end, the cap being coupled to an edge of the housing; a mounting plate coupled to the cap; a circuit board and a power supply that are mounted on a surface of the mounting plate and disposed inside the cap; a socket that is coupled to the power supply and extends through the mounting plate; an ultraviolet (UV) lamp disposed within the housing and coupled into the socket, the UV lamp being arranged to disinfect air that enters the housing before the air is expelled by the fan through the air outflow end of the housing.

According to aspects of the disclosure, a sanitizer system is provided, comprising: a housing having an air intake end and an air outflow end; a fan disposed at the air outflow end; an ultraviolet (UV) lamp disposed within the housing, the UV lamp being arranged to disinfect air that enters the housing before the air is expelled by the fan through the air outflow end of the housing; and a cap disposed at the air intake end, the cap being coupled to an edge of the housing, the cap being arranged to house a power supply that is configured to power the UV lamp.

The above and other aspects, features and advantages of the present invention will become apparent from the following description read in conjunction with the accompanying drawings, in which like reference numerals designate the same elements.

BRIEF DESCRIPTION OF THE DRAWINGS

A further understanding of the present invention can be obtained by reference to a preferred embodiment set forth in the illustrations of the accompanying drawings. Although the illustrated preferred embodiment is merely exemplary of methods, structures and compositions for carrying out the present invention, both the organization and method of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which:

FIG. 5A is a top view of the air purification system of FIG. 2A.

FIG. 5B is a bottom view of the air purification system of FIG. 2A.

FIG. 5C is a front schematic view of the air purification system of FIG. 2A.

FIG. 5D is a lengthwise cross-sectional view of the air purification system of FIG. 2A.

FIG. 1I is a partial cross-sectional side-view of the air purification system of FIG. 6, according to aspects of the disclosure.

DETAILED DESCRIPTION OF THE PREFERRED EMBODIMENTS

Figure 1:
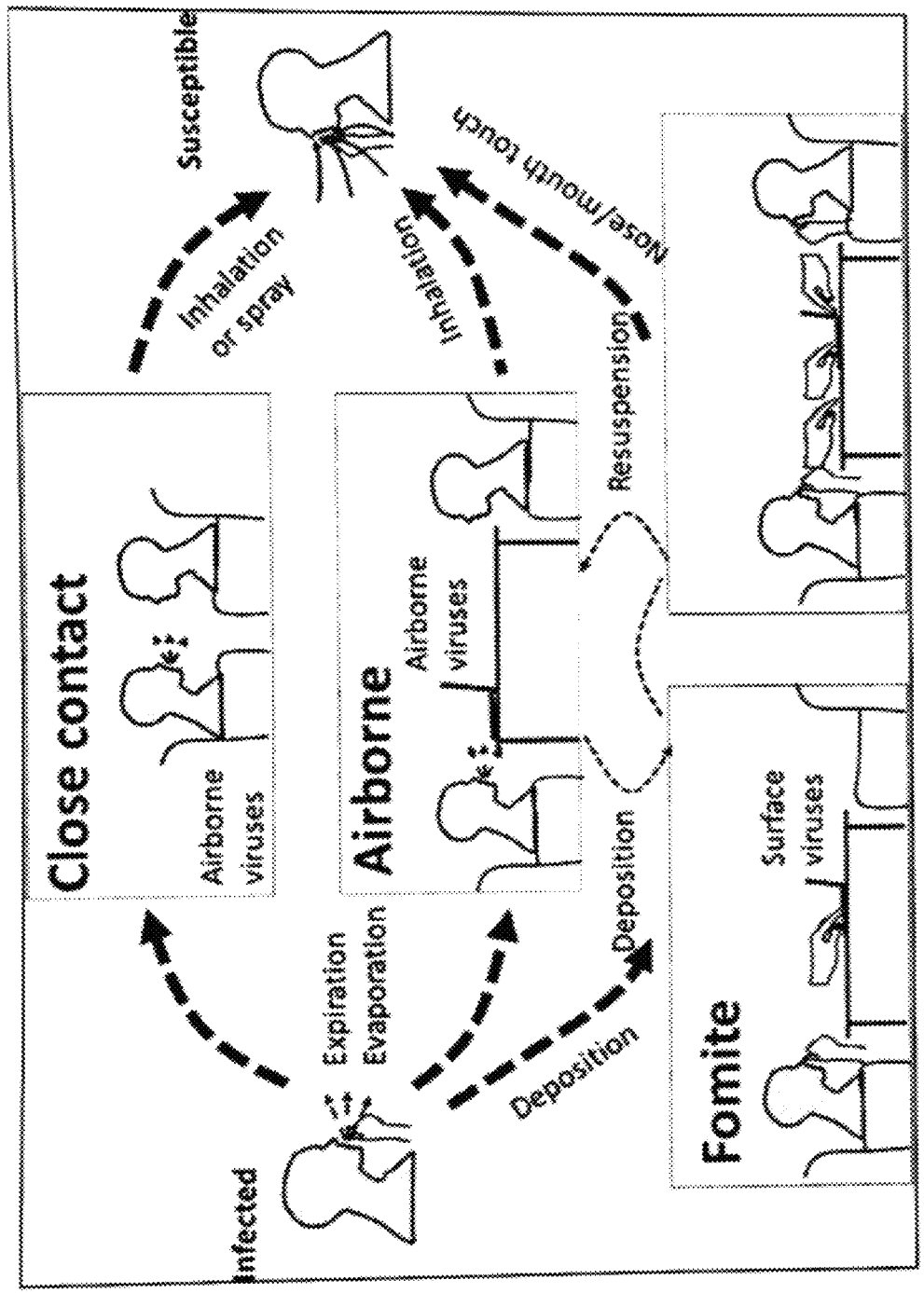
FIG. 1 is a schematic illustration showing various routes of pathogen transmission between individuals.

As required, a detailed illustrative embodiment of the present invention is disclosed herein. However, techniques, systems, compositions and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, below, etc., or motional terms, such as forward, back, sideways, transverse, etc. may be used with respect to the drawings. These and similar directional terms should not be construed to limit the scope of the invention in any manner.

An air purification system 100 will now be described with reference to FIGS. 2-5D.

The air purification system 100 is an ultraviolet jet bioaerosol disinfectant that utilizes the power of ultraviolet germicidal irradiation (i.e., UVC, to combat bioaerosol transmissions by neutralizing pathogens and bioaerosols in any breathable space, e.g., an indoor environment that includes a shared space in which multiple individuals are present. UVC is a germicidal ultraviolet wavelength of light having a wavelength between and including 100-280 nm, and most preferably at 254 nm. UVC is effective in penetrating the cell membrane breaking the DNA structure of the microorganism, which neutralizes and inhibits reproduction of the microorganism, thereby sterilizing air or surfaces that have been irradiated. Although some pathogens are more susceptible to the germicidal effects of UVC, all known microorganisms (e.g., fungus, mold, bacteria, and viruses) are destroyed with the required concentrations of UVC germicidal energy.

Natural sunlight delivers ultraviolet radiation with the ability to destroy and deactivate biological (UVC) as well as chemical contaminates (UVV) in air as well as surfaces. UVC portion of ultraviolet radiation has enough energy to break down the DNA of a microorganism thus inhibiting production. Hence, UVC is effective in destroying fungus/mold, bacteria and viruses as described under mechanism of action.

Common Microorganisms neutralized with ultraviolet germicidal irradiation (UVGI) include, for example, Bacteria, Viruses, Protozoa, Measles, tuberculosis, Dysentery bacilli, *Staphylococcus aureus*, Legionellosis, *Bacillus anthracis, Escherichia coli*, and *B. subtilis*.

The presently disclosed air purification system 100 addresses mold/bioaerosol contamination at the source including but not limited to: all public gathering places, schools, lobbies, restaurants, shopping malls, office spaces, garages, large warehouses, residential settings, hotel rooms, dormitory rooms, and is also customizable for application in a variety of applications such as but not limited to floor standing models, wall mounted models, and ceiling mounted models.

As shown in FIG. 2A, the air purification system 100 is mountable onto a ceiling surface C within a room. Persons P that are seated at a table T may be seated a distance apart from one another and may be positioned under the air purification system 100 such that air that is exhaled by the persons P is redirected by the air purification system 100 in the direction of directional arrow F through a generally cylindrical housing 102 by entering an air intake at its proximal end 102P and moving through the housing 102 where it is purified and exiting the housing 102 at its distal end 102D. A handle 104 may be coupled to the housing 102 at the distal end 102D and suspended from the ceiling C by an attachment member 106 that is coupled to the handle 104 by a cable 108. The proximal end 102P of the housing 102 may be weighted down to stabilize the housing 102 and prevent it from swinging or moving when it is suspended from the ceiling C. Depending on the characteristics of the room or space that is to be cleansed, the characteristics of the air purification system, such as the rate of air flow through the housing 102, may be adjusted to increase the efficiency of the purification of the air such that the air that exhaled from each of the persons P is largely diverted into the air purification system 100 and cleansed before it can be inhaled by persons P that are sharing the space or room.

As shown in FIG. 2B, instead of the handle 104 coupling the housing 102 may be received in a mount 103 that couples the housing 102 to the ceiling C. As shown best in FIG. 2C, the mount 103 may be generally cylindrical defining an interior space 1031 that is configured to receive and approximate the shape of the housing 102. A collar 103C may snuggly wrap around and frictionally secure the housing 102 within the mount 103. Apertures 103A may facilitate sliding of the housing 102 into the interior 1031 of the mount 103 by preventing vacuum or air pressure within the interior 1031 from building up due to the sliding of the housing 102 therethrough. In addition, the apertures 103A allow for purified air from the housing 102 to once again flow into the room or space in which the system 100 is placed.

As shown in FIG. 2C, the collar 103C may include a plurality of apertures 103A that extend through and into an interior space 1031 centrally disposed within the collar 103C. The apertures 103A are each configured to receive a fastener 103F such that when the system 100 that is disposed within the interior space 1031 is frictionally secured therein by the fasteners 103F. A plate 105 may be secured to the ceiling C and may be secured to the housing 103H of the mount 103 via a plurality of apertures 105S extending through lateral sides of the plate 105 by placing a fastener 105F into each. A plurality of apertures 105A extending through the plate 105 in the direction toward the ceiling C may secure the plate 105 to the ceiling C.

As shown in FIG. 2D, the mount 103 may be modified to replace the housing 103H and plate 105 by a mounting plate 107 that is configured to be secured to the ceiling C and a plurality of cables 107C that extend from the plate 107 and that are each coupled to the collar 103C such that the collar 103C is suspended from the plate 107 by the cables 107C.

The collar 103C may include a light source. For example, a plurality of light emitting diodes (LEDs) may be disposed on a downward facing surface of the collar 103C. The collar 103C may be electrically coupled, e.g., by a solenoid electrical connection, such that when the system 100 is inserted into the collar 103C, an electrical connection may be established.

As shown in FIG. 3, the system 100 may include a reflective and/or metallic lining, e.g., aluminum, that coats the inner wall of the housing 102. A UVC lamp 102L may be centrally disposed within the housing 102. A fan 107F may be disposed at the distal end or outlet end of the housing 102 to facilitate flow F of the air though the housing 102. A filter material 109A and/or a ballast 109 may be disposed at the proximal or inlet end of the housing 102. A ballast material to weigh down the system 100 may also be disposed at the proximal or inlet end of the system 100. An electrical or power cord E may be electrically coupled to a power outlet (not shown) to power the fan 107F and the UVC lamp 102L. The system 100 may additionally or alternatively include an internal power source, e.g., a battery.

Although the system 100 is preferably mounted on a ceiling, in some embodiments, the system 100 may be placed upon a stand 110 (FIG. 4) that includes a surface 112 on which the system 100 is placed. The surface 112 may be weighted to enhance its stability and a base 114 may rest on a floor and may be coupled in a tripod arrangement by arms 116 to the surface 112.

FIGS. 5A-5D depict the system 100 in a top view, a bottom view, a front schematic view, and a lengthwise cross-sectional view, respectively. As shown in FIGS. 5C and 5D, a filter 109A may be disposed at the air intake section of the housing 102 and a filter 109B may be disposed at the air outlet section of the housing 102. The filters 109, 109A, 109B may be formed from a HEPA filter material to facilitate capture of particles. A light source, e.g. one or more LEDs (light emitting diode) may be coupled or secured to the filter 109A or may be disposed within a portion(s) of the filter 109A without obstructing the function of the filter 109A

The efficiency of the system 100 is dependent on variety of characteristics that may be determined based on the particular characteristics of the usage case, e.g., size of room, number of occupants, etc. For example, a duct characteristics and UVGI lamp characteristics may be customized. For example, the housing 102 may have a diameter of 6 inches and the material lining of the wall 102M may be aluminum. The fan 107F may be rated to propel air through the duct of such characteristics at an airflow rate of 100 CFM (cubic feet per minute) at a velocity of 509.3 feet per minute. The lamp 102L may have a length of 457 mm and a UVGI power of 17 W such that the average germicidal UV dose delivered is 3094 microjoules per centimeter squared for an exposure time of 0.13 seconds.

Figure 6:
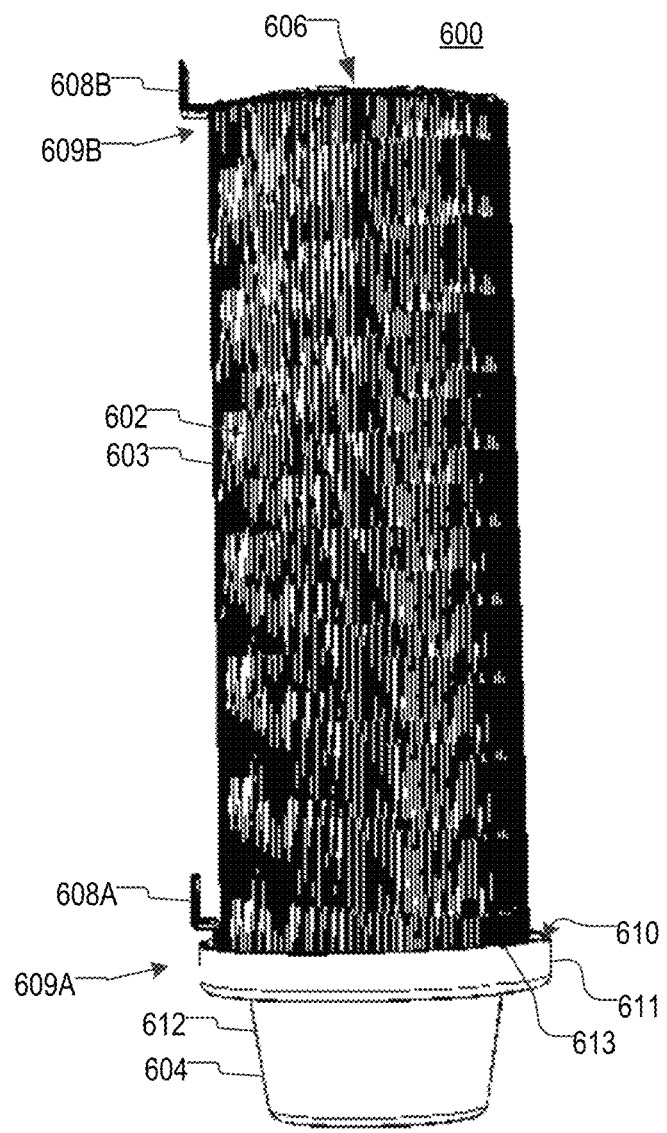
FIG. 6 is diagram of an air purification system, according to aspects of the disclosure.

FIG. 6 is a diagram of an air purification system 600, according to aspects of the disclosure. The system 600 may include a housing 602 having an air intake end 609A and an air outflow end 609B. The housing 602 may include a sidewall 603 that is arranged to define a cavity 717 (shown in FIG. 7). The sidewall 603 may be coupled to a bottom edge 710 and a top edge 720 (shown in FIG. 7) of the housing 602. The bottom edge 710 may be transverse (e.g., perpendicular) to the sidewall 603 and it may extend inwardly into the housing 602 (shown in FIG. 9). The top edge 720 may also be transverse to the sidewall 603 and it may extend inwardly into the housing 602. A cap 604 may be coupled to the bottom edge 710 of the housing 602. A fan assembly 606 may be coupled to the top edge of the housing 602. The fan assembly 606 may include a top plate 712 that is arranged to support a fan grill 713. The fan assembly 606 may also and an electric fan 714 that is disposed underneath the fan grill 713 (shown in FIG. 7).

A mounting bracket 608A may be coupled to the air intake end of the housing 602 and a mounting bracket 608B may be coupled to the air outflow end 609B of the housing 602. Each of the mounting brackets 608A-B may have a hole 711 formed therein (show in FIGS. 7 and 11). The mounting brackets 608A-B may be used to mount the system 600 on a wall (e.g., by running a respective screw throw the hole 711 of each of the mounting brackets 608A-B and driving it into wall stud). Optionally, when the system 600 is mounted on a wall of a room, the cap 604 may be facing the floor of the room and the fan assembly 606 may be facing the ceiling.

Figure 2A:
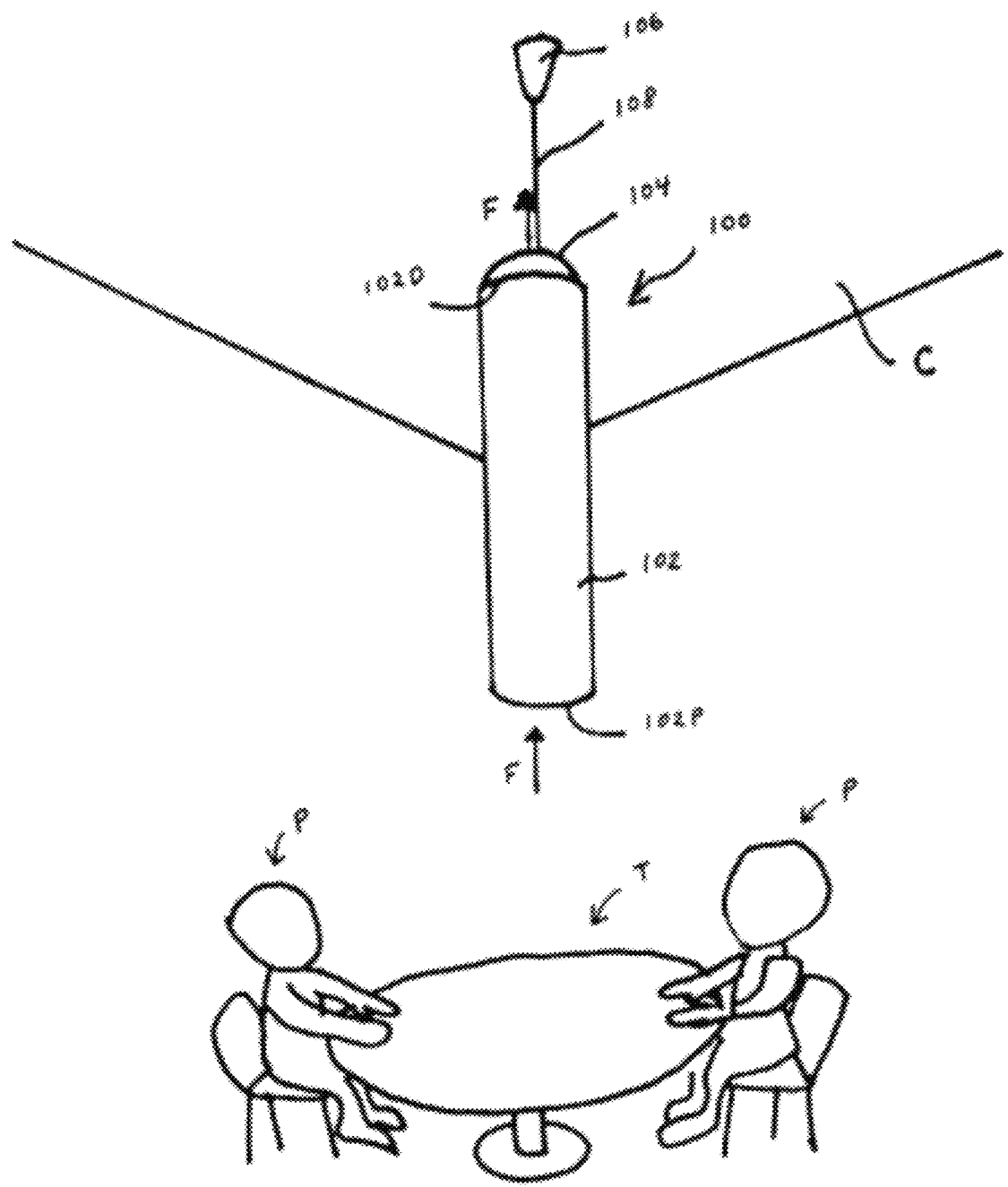
FIG. 2A is a perspective view of an air purification system in accordance with the present disclosure shown in use.
Figure 2B:
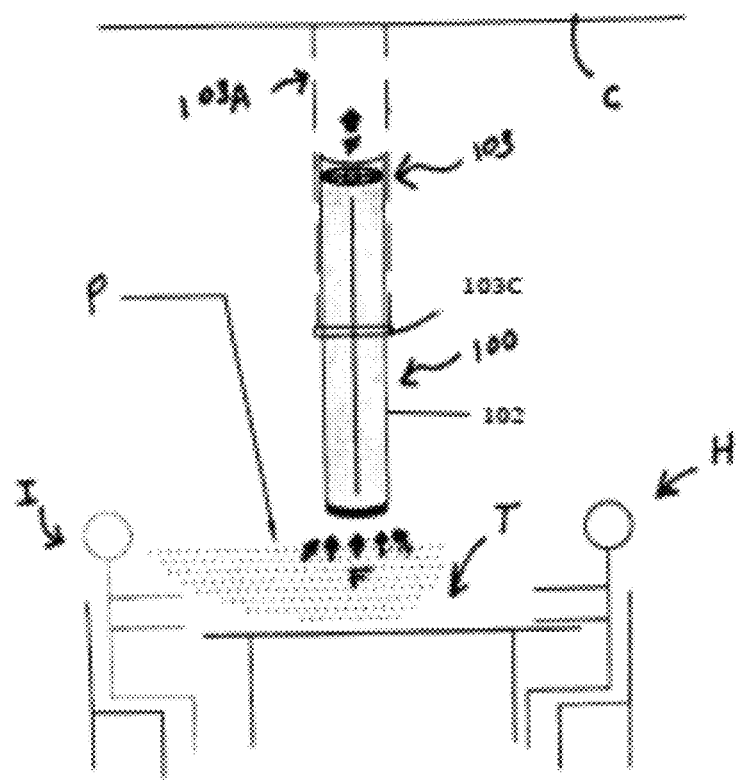
FIG. 2B is an illustration of the air purification system of FIG. 2A shown in use.
Figure 2C:
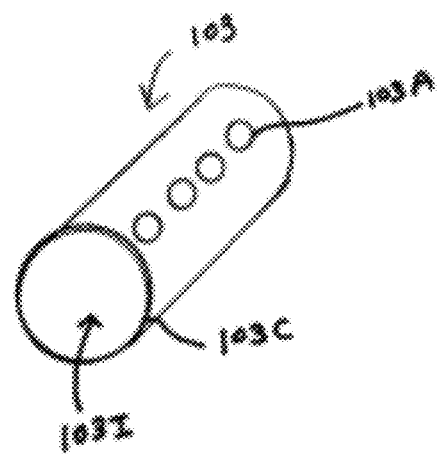
FIG. 2C is a perspective view of a ceiling mount
Figure 3:
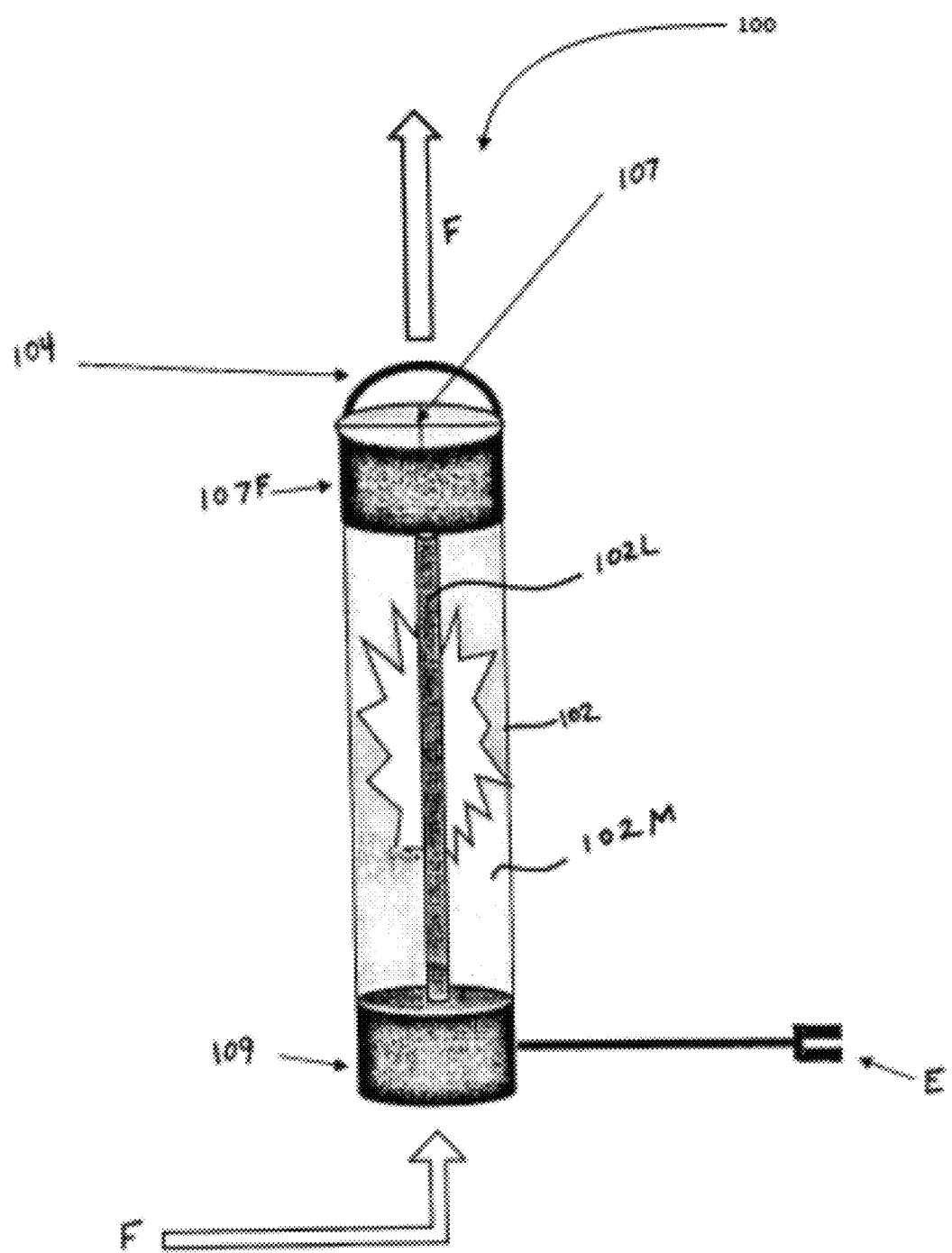
FIG. 3 is a schematic view of the air purification system of FIG. 2A.
Figure 4:
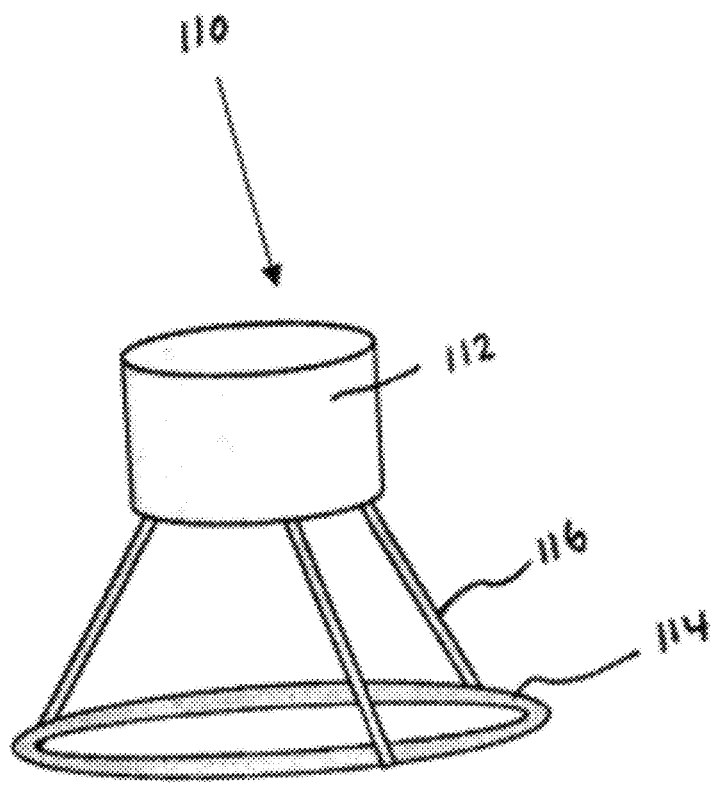
FIG. 4 is a perspective view of a stand.

Alternatively, instead of being mounted on the wall of a room, the system 600 may be hung from the ceiling of the room (see also FIG. 2A). In this regard, in one implementation, the top plate 712 may be provided with hanging brackets 715. The hanging brackets 715 may be formed on opposite ends of the top plate 712 and they may be integral with the top plate 712. Each of the hanging brackets 715 may be provided with a respective hole that is arranged to receive a cable by which the system 600 can be hung from the ceiling of a room. Optionally, when the system 600 is hung from the ceiling of a room, the cap 604 may be facing the floor of the room and the fan assembly 606 may be facing the ceiling.

Although in the present example the hanging brackets 715 are integral with the top plate 712, alternative implementations are possible in which the hanging brackets 715 are formed separately of the top plate 712. In such implementations, the hanging brackets 715 may be fastened to the top plate 712 or coupled to the sidewall 603 of the housing 602 or another component of the system 600. Stated succinctly, the present disclosure is not limited to any specific implementation of the hanging brackets 715.

Figure 9:
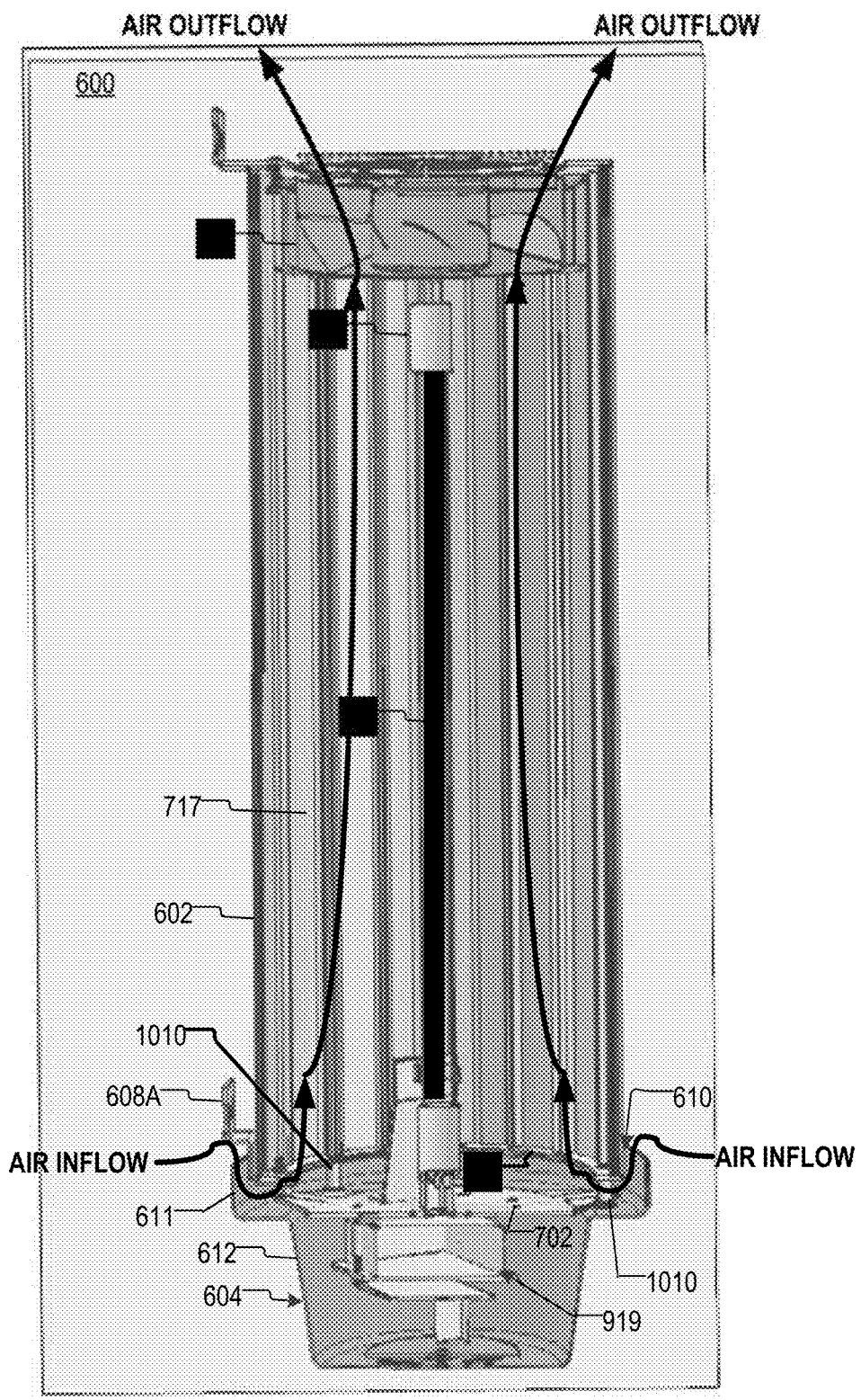
FIG. 9 is a cross-sectional side-view of the air purification system of FIG. 6, according to aspects of the disclosure.

The cap 604 may include a top portion 611 and a bottom portion 612. The top portion 611 may have a top edge 613. As illustrated in FIG. 9, the top portion 611 of the cap 604 may be arranged to receive the housing 602, such that when the housing 602 is inserted into the cap 604, the bottom edge 710 of the housing 602 is situated below the top edge 613 of the top portion 611 (of the cap 604). As a result of this arrangement, when the cap 604 is placed over the housing 602, the sidewall 603 of the housing 602 and the top portion 611 of the cap 604 may overlap.

Figure 11:
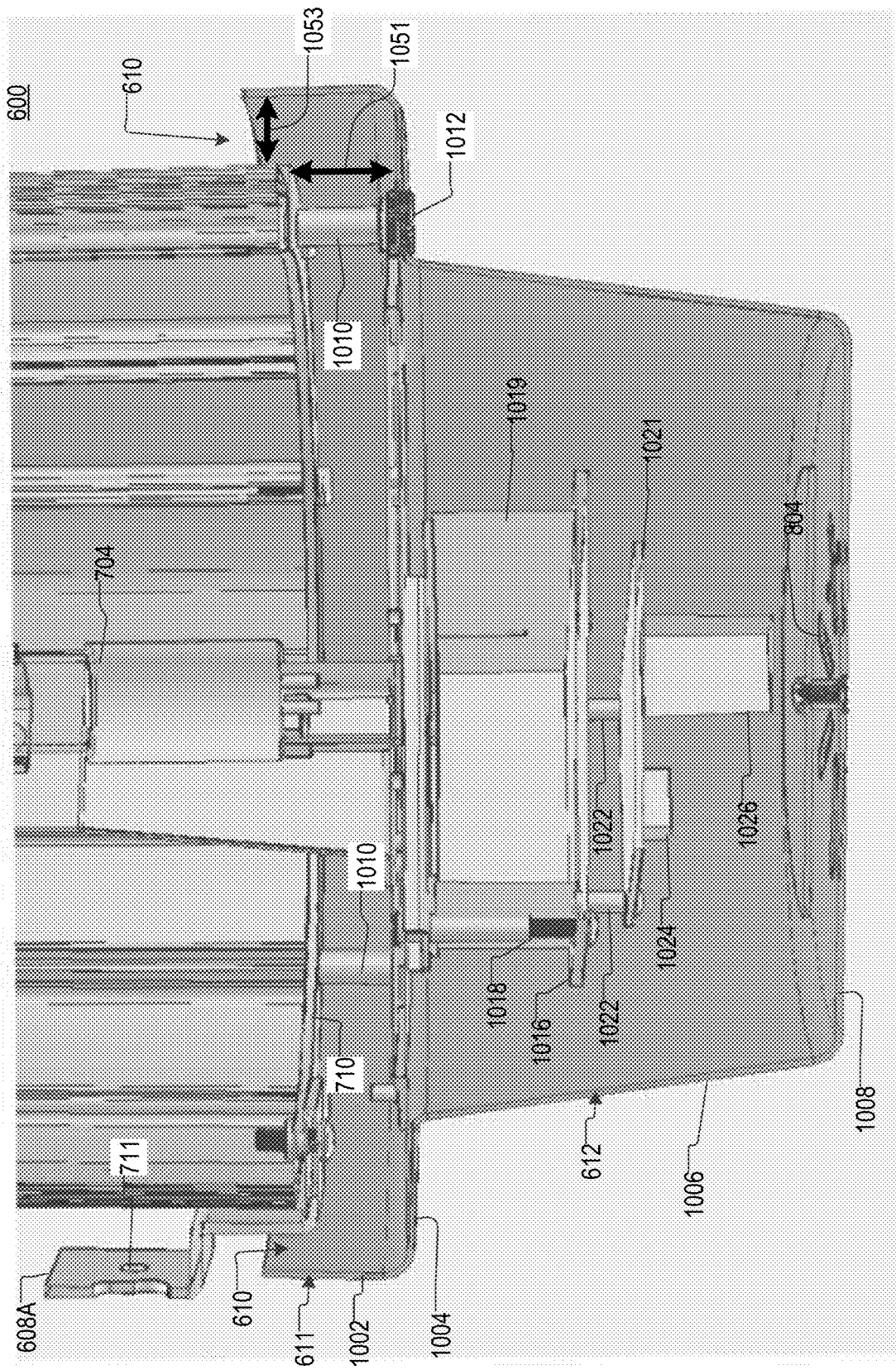

The top portion 611 of the cap 604 may include a base 1004 and a sidewall 1002. The bottom portion 612 of the cap 604 may include a sidewall 1006 (shown in FIG. 11) and a base 1008. The top portion 611 may have a circular cross-section having a first diameter. The housing 602 may have a circular cross-section having a second diameter. The first diameter may be sufficiently larger than the second diameter, so as to allow an intake port 610 to be formed between the top portion 611 of the cap 604 and the housing 602. As illustrated in FIG. 11, the intake port 610 may be defined by: (i) a gap 1053 between a sidewall 1002 of the top portion 611 and the sidewall 603, and (ii) a gap 1051 between the base 1004 of the top portion 611 and the bottom edge 710 of the housing 602.

According to the example of FIGS. 6-13, the housing 602 has a cylindrical shape. However, alternative implementations are possible in which the housing 602 has a different shape. For instance, in some implementations, the housing 602 may be shaped like the frustum of a cone. Additionally or alternatively, in some implementations, the housing 602 may be shaped as a parallelepiped. Stated succinctly, the present disclosure is not limited to any specific shape of the housing 602.

In some implementations, the housing 602 may be the same or similar to the housing 102, which is discussed above with respect to FIG. 2A. In some implementations, the housing 602 may be formed of anodized aluminum. In some implementations, the cap 604 may be formed of anodized aluminum and/or plastic. Additionally or alternatively, in some implementations, the system 600 may have a height of 71 cm and a stand footprint of 44 cm. Additionally or alternatively, in some implementations, depending on its configuration, the system 600 may weigh anywhere in the range of 5.4-6.8 kg (e.g., 5.4 kg or 6.8 kg, etc.). In some implementations, the body 602 may have a diameter of approximately 20 cm. Additionally or alternatively, in some implementations, the system 600 may include a device for odor control installed in the housing 602.

Figure 7:
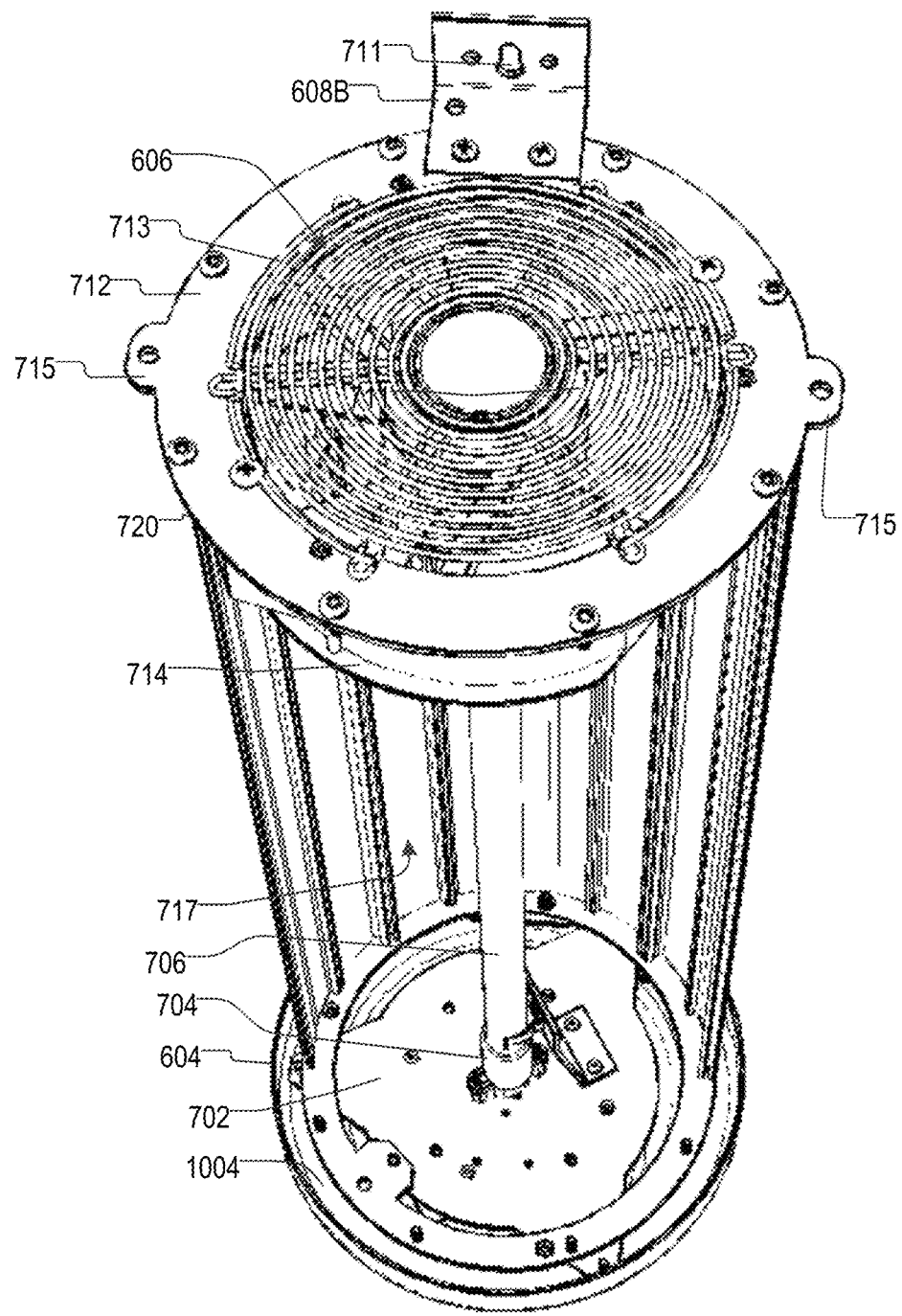
FIG. 7 is a top-down perspective view of the air purification system of FIG. 6, according to aspects of the disclosure.

FIG. 7 is a perspective bottom-down view of the system 600, according to aspects of the disclosure. FIG. 7 illustrates that a mounting plate 702 may be disposed in the cap 604. According to the present example, the mounting plate 702 may rest on the base 1004 of the top portion 611 of the cap 604. More particularly, the mounting plate 702 may be fastened to the base 1004 by one or more fasteners that are driven through the mounting plate 702 and the base 1004. A socket 704 may be mounted on the mounting plate 702. In some implementations, the socket 704 may extend through an opening in the mounting plate 702, and connect to a power supply 1019 (shown in FIG. 11), which is provided in the back of the mounting plate 702. According to the present example, the mounting plate 702 is formed of a dielectric material. However, alternative implementations are possible in which the mounting plate 702 is formed of a metal material. Additionally or alternatively, in some implementations, the mounting plate 702 may include a printed circuit board (PCB) having one or more electronic components (and/or the socket 704) installed thereon.

A UV lamp 706 may be coupled into the socket 704. The UV lamp 706 may be arranged to receive power via the socket 704. In some implementations, the UV lamp 706 may be the same or similar to the UVC lamp 102L, which is discussed above with respect to FIG. 3. The UV lamp 706 may extend lengthwise through the housing 602. A top end of the UV lamp 706 may be held securely in place by a holding bracket 913 (shown in FIG. 9). The holding bracket 913 may be coupled to the fan assembly 606 and/or to the sidewall 603 of the housing 602.

Figure 8A:
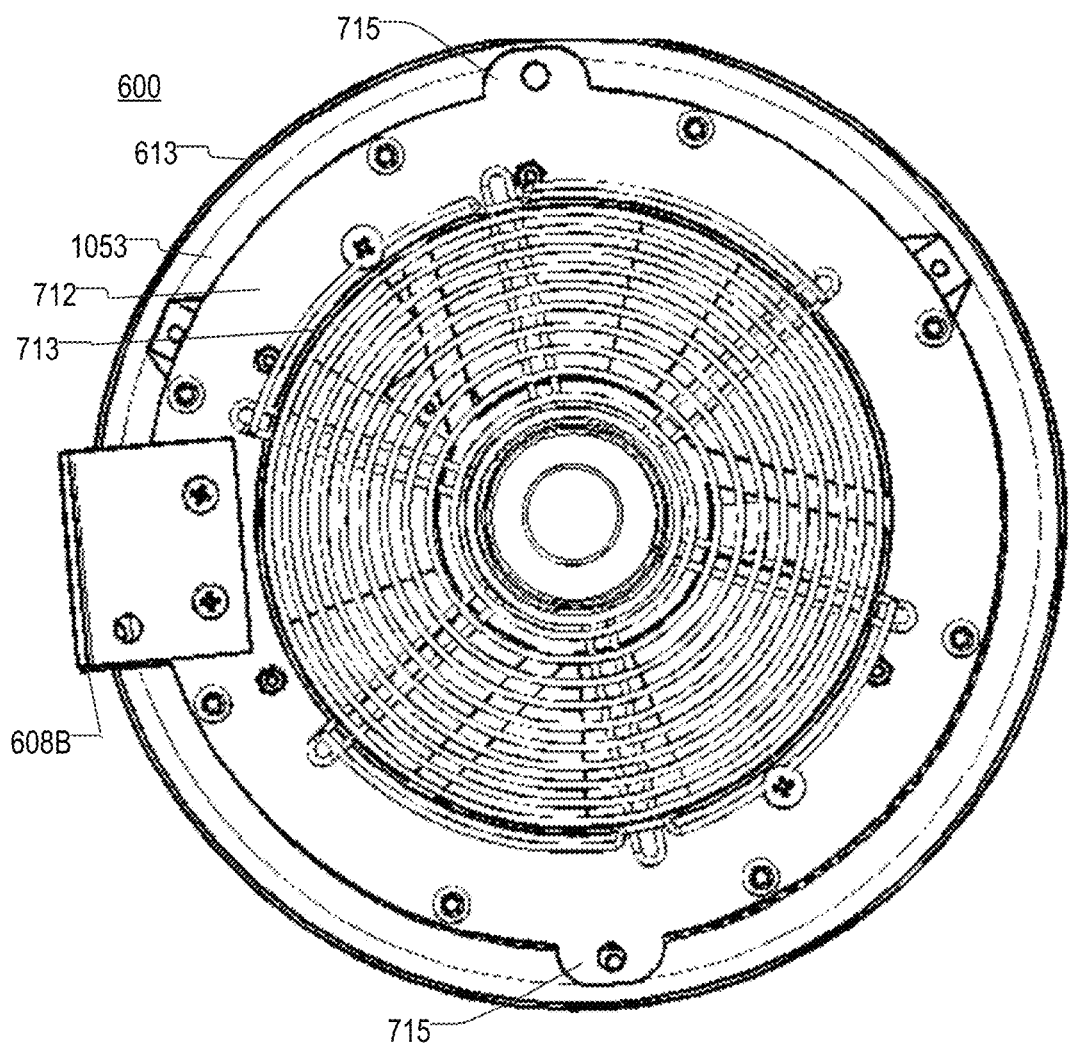
FIG. 8A is a top-down view of the air purification system of FIG. 6, according to aspects of the disclosure.

FIG. 8A is a planar top-down view of the system 600, according to aspects of the disclosure. FIG. 8A illustrates that the gap 1053 (also shown in FIG. 11) of the intake port 610 may extend around the entire circumference of the housing 602. However, alternative implementations are possible in which the gap extends around only a portion of the circumference of the housing 602. Although in the present example the intake port 610 is defined by gaps 1051 and 1053 (between the cap 604 and the housing 602), the present disclosure is not limited thereto. For example, in some implementations, the intake port 610 may include a through-hole in the cap 604 or a through-hole in housing 602. Stated succinctly, the present disclosure is not limited to any specific implementation of the intake port 610.

Figure 8B:
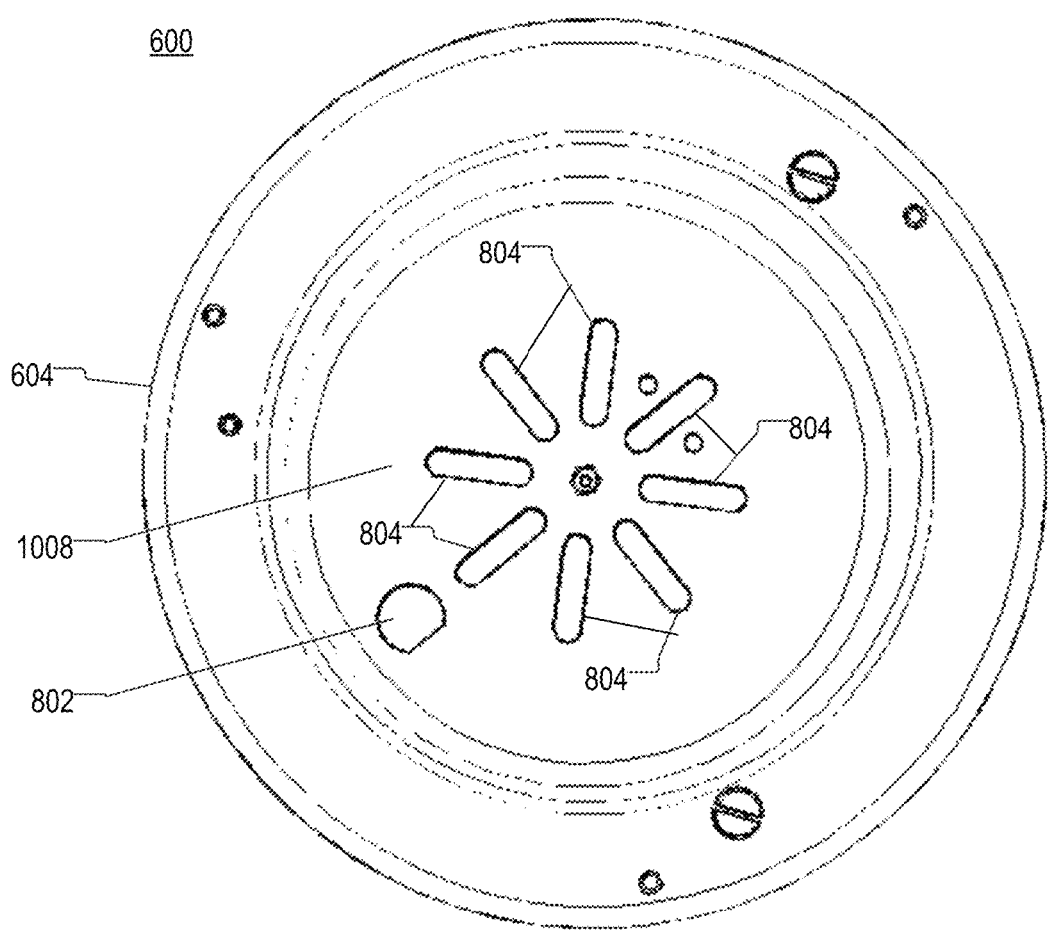
FIG. 8B is a bottom-up view of the air purification system of FIG. 6, according to aspects of the disclosure.

FIG. 8B is a planar bottom-up view of the system 600, according to aspects of the disclosure. A power button 802 may be provided on the base 1008 of the bottom portion 612 of the cap 604. As is discussed further below, the power button 802 may be coupled (or otherwise be part of) a power switch 1024 that is arranged to power the system 600 on and off. In addition, FIG. 8B illustrates that the base 1008 of the bottom portion 612 of the cap 604 may be provided with one or more apertures 804. One or more of the apertures 804 may be configured to allow light generated by a light source 1026 (shown in FIG. 11) to exit the cap 604.

FIG. 9 is a cross-sectional side view of the system 600, according to aspects of the disclosure. In one respect, FIG. 9 illustrates the flow path of air through the system 600. As illustrated, the air may enter the cavity 717 of the housing 602 through the intake port 610. While air is inside the cavity 717 the air may be irradiated by the UV lamp 706. As noted above, as a result of the irradiation, viruses and other cotangents that are carried in the air may be destroyed or deactivated. After the cavity is irradiated, the air may be expelled from the cavity 717 of the housing 602 through the fan assembly 606.

In some implementations, the UV lamp 706 may be a High Output 254 nm germicidal UV-C lamp. According to the present disclosure, it has been determined that the system 600, when using this type of lamp, can achieve a 90% reduction in the transmissivity of coronavirus (e.g., coronavirus 2), Influenza A virus and *Mycobacterium tuberculosis* in a single pass. In this regard, the system 600 provides a valuable solution for supplementing the ventilation of indoor spaces by quietly and effectively capturing and neutralizing airborne biological contaminants (e.g., bacteria, viruses, fungi, etc.), including those carried in airborne aerosol particles.

Table 1 below lists different inactivation rates that can be achieved by the system 600. The inactivation rates have been measured experimentally by using a 30" T6 High Output 254 nm UV-C lamp and a 0.2032 diameter of the body 602 (i.e., duct size of 0.2032 m) at 200 CFM airflow through the body 602:

TABLE 1

| Pathogen | Minimum Inactivation Rate | Average Inactivation Rate | Log Reduction Average |
|---|---|---|---|
| Influenza A Virus | 93.06% | 98.00% | 1 |
| MRSA | 99.32% | 99.93% | 3 |
| Mycobacterium Tuberculosis | 99.17% | 00.91 | 3 |
| Coronavirus | 99.97 | 99.999% | 5 |

Table 2 below lists different inactivation rates that can be achieved by the system 600. The inactivation rates have been measured experimentally by using a 30" T6 High Output 254 nm UV-C lamp and a 0.2032 m diameter of the body 602 (i.e., duct size of 0.2032 m) at 150 CFM airflow through the body 602:

TABLE 2

| Pathogen | Minimum Inactivation Rate | Average Inactivation Rate | Log Reduction Average |
|---|---|---|---|
| Influenza A Virus | 91.83% | 97.7% | 1 |
| MRSA | 99.08% | 99.91% | 3 |
| Mycobacterium Tuberculosis | 99.97% | 99.999% | 3 |
| Coronavirus | 99.97 | 99.999% | 5 |

FIG. 9 further illustrates that the configuration of intake port 610 causes the air to travel in an S-shaped path when entering the cavity 717 of the housing 602. This configuration, ideally prevents (or at least hinders) UV light that is generated by UV lamp 706 from exiting the housing 602, and irradiating any persons that might be in the vicinity of the system 600. As is well-known, excessive UV radiation may be harmful to the human health. Accordingly, containing any UV light that is generated by the UV lamp 706 within the cavity 717 of the housing 602 is advantageous because it increases the overall safety of operation of the system 600.

FIG. 9 further illustrates that the socket 704 (and/or UV lamp 706) may be raised relative to the gap 1051 of the intake port 610. This may prevent (or at least hinder) UV light from being emitted (by the UV lamp 706) directly into the gap 1051 of the intake port 610 and subsequently reflected out of the housing 602.

FIG. 9 further illustrates that electronic circuitry 919 may be provided in the bottom portion 612 of the cap 604. The electronic circuitry 919 may include any suitable type of electronic circuitry for controlling the operation of the system 600. The electronic circuitry 919 may be at least in part supported by the mounting plate 702. One possible implementation of the electronic circuitry 919 is discussed further below with respect to FIG. 11.

Figure 10:
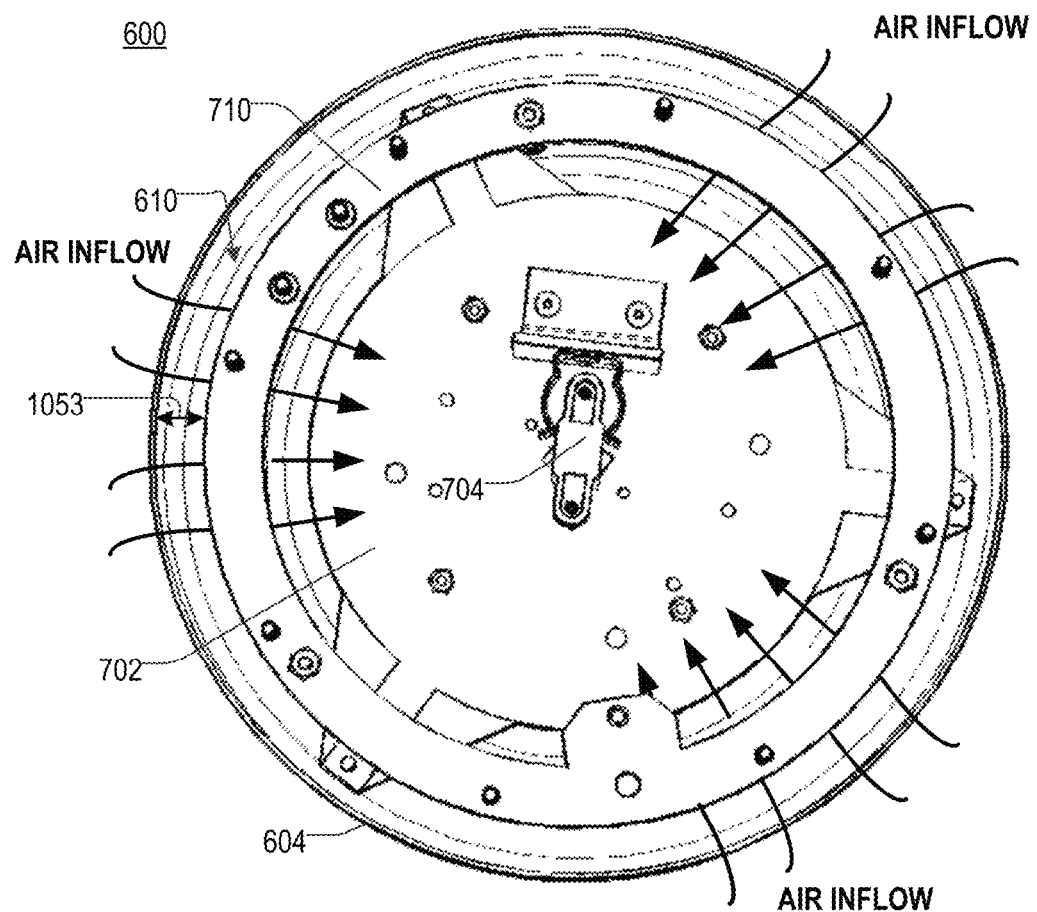
FIG. 10 is a top-down view of the air purification system of FIG. 6, according to aspects of the disclosure.

FIG. 10 is a planar top-down view of the system 600, with the fan assembly 606 removed. FIG. 10 is provided to show the flow of air into the cavity 717 from another angle. As illustrated, the air may travel through the gap 1053 between the cap 604 and the sidewall 603, under the bottom edge 710 of the housing 602, and into the cavity 717 of the housing 602. The air may be drawn into the cavity 717 of the housing 602 by the action of the fan 714.

FIG. 11 is a partial cross-sectional view of the system 600, according to aspects of the disclosure. FIG. 11 illustrates in further detail the coupling between the cap 604 and the housing 602. As noted above, the top portion 611 of the cap 604 may include a sidewall 1002 and a base 1004. A plurality of spacers 1010 may be disposed between the base 1004 and the bottom edge 710 of the housing 602. As is known in the art, each of the spacers 1010 may include a (cylindrical) object having a bore formed therein. The function of the spacers 1010 is to prevent the bottom edge 710 of the housing 602 from being pressed against the base 1004 of the top portion 611 of the cap 604. In other words, the purpose of the spacers 1010 is to create the gap 1051. As noted above, the gap 1051 allows air to flow into cavity 717 of the housing 602. The housing 602 and the cap 604 may be coupled by a plurality of fasteners 1012. Each fastener 1012 may be disposed in a respective hole (e.g., a through hole) in the base 1004, the respective bore in one of the spacers 1010, and a respective hole (e.g. a through hole) in the base 1004 of the top portion 611 of the cap 604.

FIG. 11 illustrates in further detail one possible configuration of the electronic circuitry 919. According to the example of FIG. 11, the electronic circuitry 919 may include a power supply 1019 and a control board 1021. According to the present example, the UV lamp 706 includes a fluorescent UV light tube, and the power supply 1019 includes a ballast for regulating the current that is being supplied to the UV lamp 706. However, it will be understood that the present disclosure is not limited to any specific type of light source and light source power supply being used. For example, in some implementations, the UV lamp may include one or more UV LEDs and the power supply 1019 may include circuitry for powering the UV LEDs.

The control board 1021 may include any suitable type of electronic circuitry for controlling the operation of the system 600. In some implementations, the control board 1021 may include a power switch 1024 and a light source 1026. The power switch 1024 may be mechanically or electrically coupled to the power button 802, and it may be configured to turn the system 600 on and off. The light source 1026 may be configured to project light outwardly from the cap 604 through the apertures 804. According to the present example of light source 1026 includes one or more light-emitting diodes (LEDs). However, the present disclosure is not limited to any specific type of light source. In some implementations, the light output of the light source 1026 may be 150 lumens or greater. In this regard, it will be understood that the provision of the light sources 1026 in the system 600 may allow the system 600 to double as a light fixture. Additionally or alternatively, in some implementations, the light source may be a status light. Additionally or alternatively, in some implementations, the light source 1026 may be omitted.

The power switch 1024 may be used to turn the system 600 on and off. For example, when the power switch 1024 is pressed, the UV lamp 706, the fan 714, and the light source 1026 may be turned on. When the power switch 1024 is pressed for a second time, the UV lamp 706, the fan 714, and the light source 1026 may be turned off. In some implementations, each of the fan 714, the UV lamp 706, and light source 1026 may be controlled separately from the rest. In such implementations, a separate switch (or a separate switching mechanism, or a separate control logic) may be provided for turning on and off (or otherwise adjusting the operation of) each of the fan 714, the UV lamp 706, and the light source 1026.

Additionally or alternatively, in some implementations, the control board 1021 may include a controller and a remote control circuit. The controller may be configured to adjust the speed of the fan 714 based on signals received from the remote-control circuit. The remote-control circuit may include an infrared (IR) sensor that is exposed through one of the apertures 804. In some implementations, the controller may be configured to turn off or dim the light source 1026. In some implementations, the controller may dim the light source 1026 in response to a signal that is received from the remote-control circuit.

In another respect, FIG. 11 illustrates in further detail how the electronic circuitry 919 is mounted inside the cap 604. As illustrated, a plate 1016 may be coupled to the mounting plate 702 via a plurality of fasteners 1018 (only one of which is shown in FIG. 11). The plate 1016 may be sufficiently spaced from the mounting plate 702 to allow a power supply 1020 to fit in the space between the mounting plate 702 and the plate 1016. The plate 1016 may include a plank of non-conductive (and/or conductive material). In some implementations, the plate 1016 may be arranged to provide mechanical support for the power supply 1020. The control board 1021 may be coupled to the plate 1016 by fasteners 1022 (two of which are shown in FIG. 11).

Figure 12:
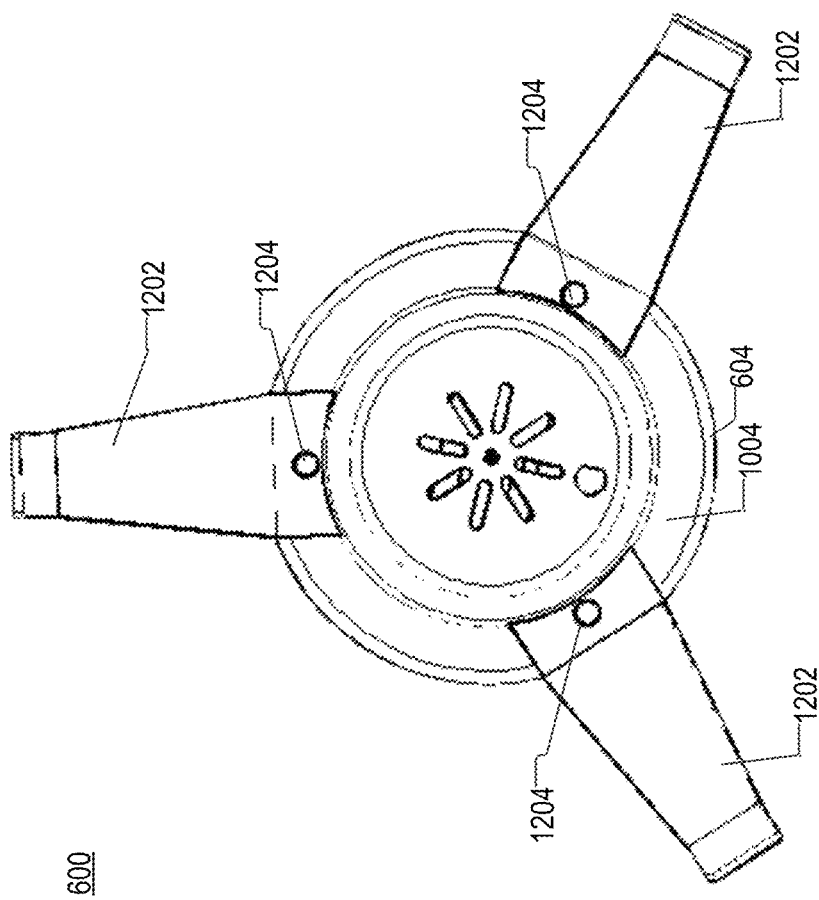
FIG. 12 is a bottom-up side view of an air purification system, according to aspects of the disclosure.
Figure 13:
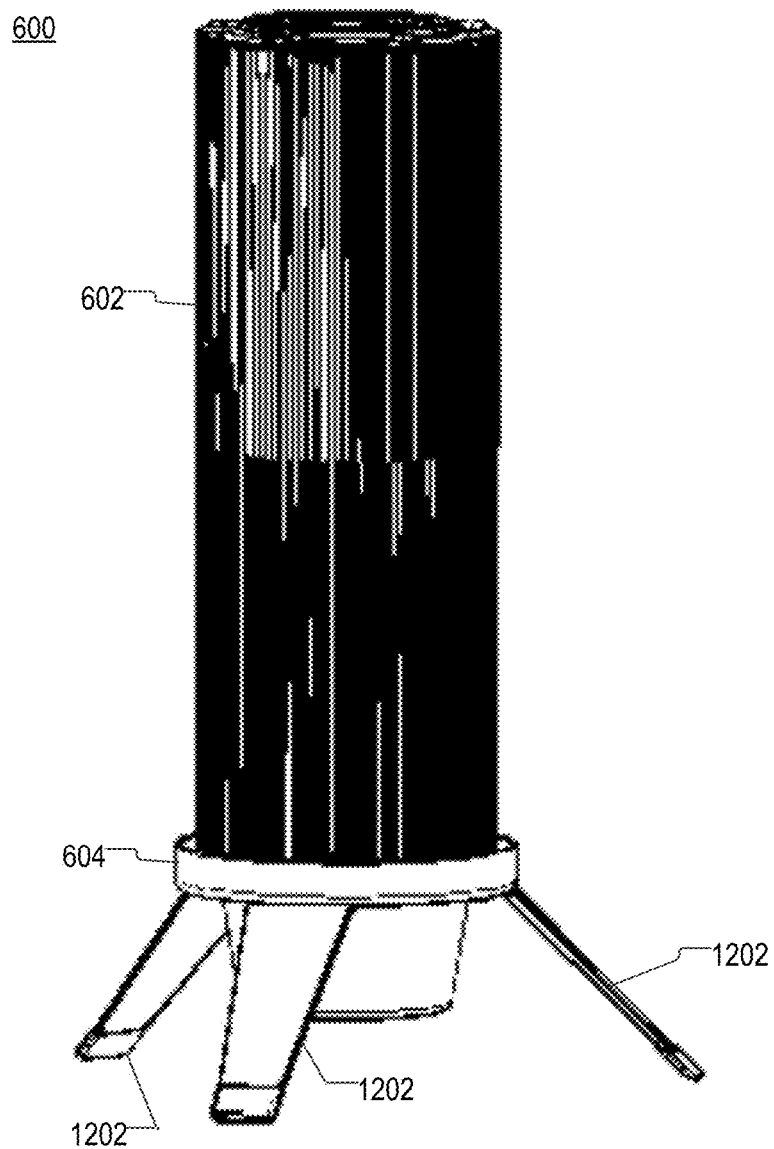
FIG. 13 is a side view of the air purification system of FIG. 12, according to aspects of the disclosure.

FIGS. 12-13 show the system 600 in accordance with another implementation. In this implementation, the system 600 is provided with legs 1202 which may be used to stand the system 600 on the ground. According to the example of FIGS. 12-13, each of the legs 1202 is coupled to the base 1004 of the cap 604 via a respective fastener 1204. However, it will be understood that the present disclosure is not limited to any specific method for coupling the legs 1202 to the rest of the system 600.

Figure 14A:
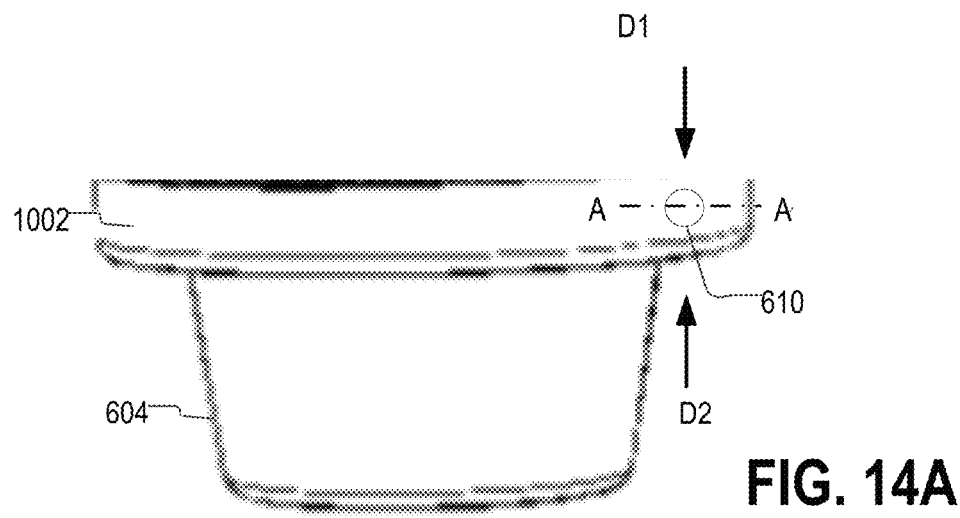
FIG. 14A is diagram of an example of a cap, according to aspects of the disclosure.
Figure 14B:
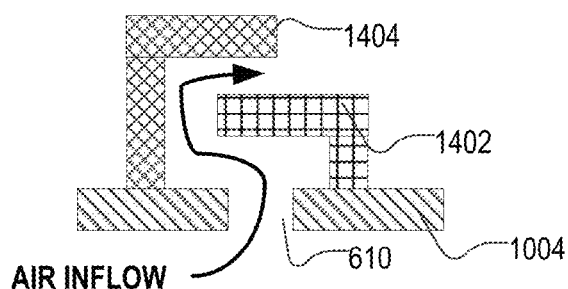
FIG. 14B is a cross-sectional view of barriers for forcing air to travel in an S-shaped path, according to aspects of the disclosure.
Figure 14C:
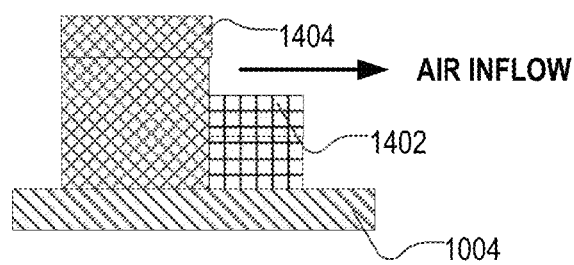
FIG. 14C is a top-down view of barriers for forcing air to travel in an S-shaped path, according to aspects of the disclosure.
Figure 14D:
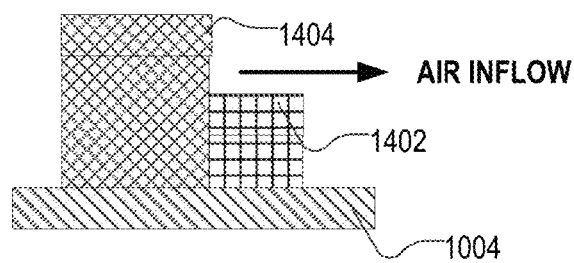
FIG. 14D is a bottom-up view of barriers for forcing air to travel in an S-shaped path, according to aspects of the disclosure.

FIGS. 14A-D illustrate another implementation of the intake port 610. In the example of FIGS. 14A-D, the intake port 610 is implemented as a through-hole that is formed in the sidewall 1002 of the cap 604. FIG. 14B is a cross-sectional side view of a portion of the cap 604, that is taken along axis A-A. FIG. 14B illustrates that the intake port 610 is provided with barriers 1402 and 1404, which force air to travel in an S-shaped path when entering the cavity 717 of the housing 602. The provision of the barriers 1404 and 1402 is advantageous because it may allow air to enter the housing 602 while preventing UV light generated by the UV lamp 706 from exiting the housing. FIG. 14A. FIG. 14C is a top-down view of the barriers 1402 and 1404. FIG. 14C shows the barriers 1402 and 1404 when viewed from direction D1. FIG. 14D is a bottom-up view of the barriers 1402 and 1404. FIG. 14C shows the barriers 1402 and 1404 when viewed from direction D2. Together, FIGS. 14C-D illustrate that the barriers 1402 and 1404 may be implemented as parallelepipeds, which have only one side removed, and which are nested into each other. In the example of FIGS. 14C-D, barrier 1402 is nested into barrier 1404, such that the open side of the barrier 1402 is situated entirely inside barrier 1404.

FIGS. 14A-B are provided as an example only. Those of ordinary skill in the art will readily recognize, after reading this disclosure, that there are various ways to force air to travel an S-shaped path to allow the air to enter the housing 602 while eliminating or reducing the amount of UV light that exits the housing 602 from the opening that is used by the air to enter. It will be understood that the present disclosure is not limited to any specific method for forcing air to travel in an S-shaped path. Furthermore, although in the example of FIG. 14A-B the intake port 610 is formed in the cap 604, alternative implementations are possible in which the intake port 610 is formed in the sidewall 603. In such implementations, barriers 1402 and 1404 may be provided on the back of the sidewall 603.

Having described at least one of the preferred embodiments of the present invention with reference to the accompanying drawings, it is to be understood that such embodiments are merely exemplary and that the invention is not limited to those precise embodiments, and that various changes, modifications, and adaptations may be effected therein by one skilled in the art without departing from the scope or spirit of the invention as defined in the appended claims. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A sanitizer system, comprising:
a housing having an air intake end and an air outflow end;
a fan disposed at the air outflow end;
a cap disposed at the air intake end, the cap being coupled to an edge of the housing, the cap being spaced apart from the housing so that an intake port is formed between the cap and the housing; and
an ultraviolet (UV) lamp disposed within the housing, the UV lamp being arranged to disinfect air that enters the housing through the intake port before the air is expelled by the fan through the air outflow end of the housing,
wherein the cap includes at least one intake port that includes a first barrier and a second barrier, the first and second barriers being configured as parallelepipeds that are nested into each other and define an airflow path.

2. The sanitizer system of claim 1, wherein:
the cap includes a top edge and the housing includes a bottom edge, and
the housing is partially inserted into cap, such that the top edge of the cap is positioned above the bottom edge of the housing, while a gap remains between the top edge of the cap and a sidewall of the housing.

3. The sanitizer system of claim 1, further comprising one or more spacers disposed between the housing and the cap, the one or more spacers being arranged to space the cap apart from the housing, so that the intake port is formed between the cap and the housing.

4. The sanitizer system of claim 1, wherein the intake port extends around an entire circumference of the housing.

5. The sanitizer system of claim 1, further comprising:
a mounting plate coupled to the cap;
electronic circuitry that is mounted on a surface of the mounting plate and disposed inside the cap;
a socket that is coupled to the electronic circuitry and the UV lamp, the socket extending through an opening in the mounting plate.

6. The sanitizer system of claim 1, further comprising a power supply that is arranged to power the UV lamp, the power supply being disposed in the cap.

7. The sanitizer system of claim 1, further comprising electronic circuitry that is configured to control the fan, the electronic circuitry being disposed in the cap.

8. The sanitizer system of claim 1, further comprising one or more light sources that are disposed in the cap and configured to project light outwardly from the cap.

9. The sanitizer system of claim 1, further comprising at least two mounting brackets for mounting the sanitizer system onto a wall.

10. The sanitizer system of claim 1, further comprising at least two hanging brackets for hanging the sanitizer system from a ceiling.

11. The sanitizer system of claim 1, further comprising a plurality of legs that are coupled to the cap for standing the sanitizer system onto a floor.

12. A sanitizer system, comprising:
a housing having an air intake end and an air outflow end;
a fan disposed at the air outflow end;
an ultraviolet (UV) lamp disposed within the housing, the UV lamp being arranged to disinfect air that enters the housing before the air is expelled by the fan through the air outflow end of the housing; and
a cap disposed at the air intake end, the cap being coupled to an edge of the housing, the cap being arranged to house a power supply that is configured to power the UV lamp
wherein the cap includes at least one intake port that includes a first barrier and a second barrier, the first and second barriers being configured as parallelepipeds that are nested into each other and define an airflow path.

13. The sanitizer system of claim 12, wherein the at least one intake port that is arranged to cause the air to travel in an S-shaped path when entering the housing or a specific portion of the housing.

14. A sanitizer system, comprising:
a housing having an air intake end and an air outflow end;
a fan disposed at the air outflow end;
a cap disposed at the air intake end, the cap being coupled to an edge of the housing;
a mounting plate coupled to the cap;
a circuit board and a power supply that are mounted on a surface of the mounting plate and disposed inside the cap;
a socket that is coupled to the power supply and extends through the mounting plate;
an ultraviolet (UV) lamp disposed within the housing and coupled into the socket, the UV lamp being arranged to disinfect air that enters the housing before the air is expelled by the fan through the air outflow end of the housing,
wherein the cap includes at least one intake port that includes a first barrier and a second barrier, the first and second barriers being configured as parallelepipeds that are nested into each other and define an airflow path.

15. The sanitizer system of claim 14, further comprising at least two mounting brackets for mounting the sanitizer system onto a wall.

16. The sanitizer system of claim 14, further comprising at least two hanging brackets for hanging the sanitizer system from a ceiling.

17. The sanitizer system of claim 14, further comprising a plurality of legs that are coupled to the cap for standing the sanitizer system onto a floor.

\* \* \* \* \*